(12) United States Patent
Fan et al.

(10) Patent No.: US 12,042,220 B2
(45) Date of Patent: Jul. 23, 2024

(54) LASER-ASSISTED TUMOR LOCALIZATION AND RESECTION DEVICE

(71) Applicant: Ning Fan, Qingdao (CN)

(72) Inventors: Ning Fan, Qingdao (CN); Chao Yang, Qingdao (CN); Lin Ma, Qingdao (CN); Jinzhen Cai, Qingdao (CN); Feifei Wang, Qingdao (CN); Bin Wei, Qingdao (CN); Yuan Guo, Qingdao (CN); Huan Liu, Qingdao (CN); Xiaoyue Fu, Qingdao (CN); Xin Wang, Qingdao (CN); Yong Zhang, Qingdao (CN); Wenjuan Sun, Qingdao (CN)

(73) Assignee: Ning Fan, Qingdao (CN)

( * ) Notice: Subject to any disclaimer, the term of this patent is extended or adjusted under 35 U.S.C. 154(b) by 0 days.

(21) Appl. No.: 17/809,545

(22) Filed: Jun. 28, 2022

(65) Prior Publication Data

US 2023/0301717 A1    Sep. 28, 2023

(30) Foreign Application Priority Data

Mar. 23, 2022 (CN) .......................... 202210284068.1

(51) Int. Cl.
*A61B 18/20* (2006.01)
*A61B 17/00* (2006.01)
*A61B 18/00* (2006.01)

(52) U.S. Cl.
CPC .... *A61B 18/20* (2013.01); *A61B 2017/00991* (2013.01); *A61B 2018/00601* (2013.01)

(58) Field of Classification Search
CPC ...................................................... A61B 18/20
USPC .......................................................... 606/14
See application file for complete search history.

(56) References Cited

U.S. PATENT DOCUMENTS 11,089,969 B2 *    8/2021    Chachisvilis .......... A61B 5/441

* cited by examiner

*Primary Examiner* — Nadia A Mahmood
(74) *Attorney, Agent, or Firm* — Au Law Office, P.C.; Yiu F. Au

(57) ABSTRACT

The invention discloses a laser-assisted tumor localization and resection device, which comprises a laser displacement sensor, a cylindrical base, a joint part, a transmission rod, and a data screen, wherein the laser displacement sensor comprises 2 sensors L1 and L2, which are revolvably arranged in the cylindrical base and are coaxial, mounting holes are arranged on both sides of the cylindrical base, the transmission rod is revolvably connected with the cylindrical base at multiple angles through the joint part, the data screen is arranged on the transmission rod. The invention belongs to the field of open surgery or minimally invasive surgery, in particular relates to a laser-assisted tumor localization and resection device that the surgeons use in the minimally invasive surgery and the open surgery to realize the real-time precise intraoperative navigation and tumor localization, ensure the correct surgical plane and enough tumor resection margin and improve the operation efficiency and precision.

3 Claims, 4 Drawing Sheets

LASER-ASSISTED TUMOR LOCALIZATION AND RESECTION DEVICE

RELATED APPLICATIONS

This application claims priority to China Patent Application No. 202210284068.1, filed Mar. 23, 2022; the above-identified application is hereby incorporated by reference herein.

TECHNICAL FIELD

The invention belongs to the field of open surgery or minimally invasive surgery, in particular relates to a laser-assisted tumor localization and resection device.

BACKGROUND ART

The intraoperative real-time localization of tumors in the solid organs is a surgical challenge, involving tumor resection in the liver, pancreas, lung, head, kidney, and other solid organs. The tumors are small and deep inside the organs, so that the location and depth of the tumors cannot be determined by the naked eye and touch. In this case, three problems exist in the surgery, especially in the minimally invasive surgery: 1) how to precisely pinpoint the location of the tumor; 2) how to precisely determine the incision point, angle, and depth in the surgery; 3) how to precisely implement the resection path (including how to measure the incision angle and the real-time incision distance and at what distance critical conduits will appear) planned preoperatively.

Facing the above three problems, the only tool available intraoperatively is the ultrasonic apparatus, which is used to identify the projection points of tumors and critical conduit structures on the surfaces of the organs. Just like the truth of "a tip of the iceberg," the identification on the surface is only superficial localization. After incising, the incision of the rear section plane is often too close to the deep tumor, and the accuracy of further ultrasonic examination is decreased due to gas filling. Therefore, there is no method to precisely guide surgeons in real time to dissect the organ parenchyma by the resection path planned preoperatively. Deviation of the dissection section will lead to insufficient tumor resection margin, cause damage to the tumor or large conduits and other adverse events. At present, there is no real-time intraoperative navigation system that can successfully solve the above problems to guide the surgeons in determining the first incision point, the incision angle and the resection depth and direction of each incision to ensure the correct plane planned preoperatively and determine the incision distance on the plane to reach the deepest point planned preoperatively.

These surgical challenges can be solved by a method and a device. The method is a trigonometric model-based surgical plan and system (CN 112245006 B). The method needs to be implemented precisely by equipment. Currently, there is no similar equipment. A laser-assisted tumor localization and resection device is designed to assist in implementing the method.

SUMMARY OF THE INVENTION

In view of the above problems, to overcome the defects of the prior art, the invention provides a laser-assisted tumor localization and resection device that the surgeons use in the minimally invasive and open surgeries to locate the tumors precisely in real-time, ensure the correct surgical plane and enough tumor resection margin, and improve the operation efficiency and precision.

The invention adopts the following technical proposal: the laser-assisted tumor localization and resection device comprises a laser displacement sensor, a cylindrical base, a joint part, a transmission rod and a data screen, wherein the laser displacement sensor comprises a sensor L1 and a sensor L2, which are revolvably arranged in the cylindrical base and are coaxial, the laser displacement sensor is turned on by rotating L2, mounting holes are arranged on both sides of the cylindrical base to fix the cylindrical base on the surface of the parenchymatous organ by seaming or clipping or other ways according to the toughness of the organ parenchyma, the transmission rod is revolvably connected with the cylindrical base in multiple angles through the joint part, the data screen is arranged on the transmission rod, and the transmission rod is connected with the cylindrical base through the joint part, and can be moved along with the organ motion and turning due to the presence of the joint when the cylindrical base is fixed to the surface of the organ.

Further, a line connected with the laser displacement sensor is arranged in the transmission rod and is connected with the in vitro data screen through the transmission rod and the data screen displays the beam ranging of the sensor L1 and the sensor L2 and the real-time value of the included angle.

Further, the cylindrical base is hollow cylindrical, and is 2-4 cm long.

Further, a telescopic rod is arranged in the cylindrical base, and the sensor L1 and the sensor L2 are coaxially arranged on the telescopic rod, and the rotatable sensor L2 can be put together with the sensor L1 to be contained in the cylindrical base, facilitating the whole device to pass through the trocar hole.

Further, the data screen is provided with a rotary disk connected with a rotary drive device arranged on the L2 sensor.

Further, a locking button is arranged on the transmission rod to lock and release the joint part.

Further, the laser displacement sensor is ZLDS10X or ZLDS11X laser displacement sensor, which is 1-2 cm long.

The invention has the following beneficial effects: a laser-assisted tumor localization and resection device of the proposal is designed based on the triangular model to assist in the implementation of the method, the laser does not directly locate the tumor but locates the triangular model containing the tumor, and surgeons use the tool to locate the tumors precisely in real-time in the minimally invasive and open surgeries, thereby ensuring correct surgical plane and enough tumor resection margin, and improving the operation efficiency and precision.

Wherein, 1. Laser displacement sensor, 2. Cylindrical base, 3. Joint part, 4. Transmission rod, 5. Data screen, 6. Sensor L1, 7. Sensor L2, 8. Mounting hole, 9. Telescopic rod, 10. Locking button, 11. Rotary disk, A. In vivo, B. Abdominal wall, C. In vitro.

The drawings are provided for further understanding of the invention. They form part of the specification and are used to explain the invention together with its embodiments and do not constitute a limitation on the invention.

EMBODIMENTS

The technical proposal in the embodiments of the invention is clearly and completely described below in combination with the drawings in the embodiments of the invention. Obviously, the described embodiments are only part of the embodiments of the invention, but not all embodiments. Based on the embodiments of the invention, all other embodiments obtained by ordinary technicians in the field without creative labor are within the scope of protection of the invention.

Figure 1:
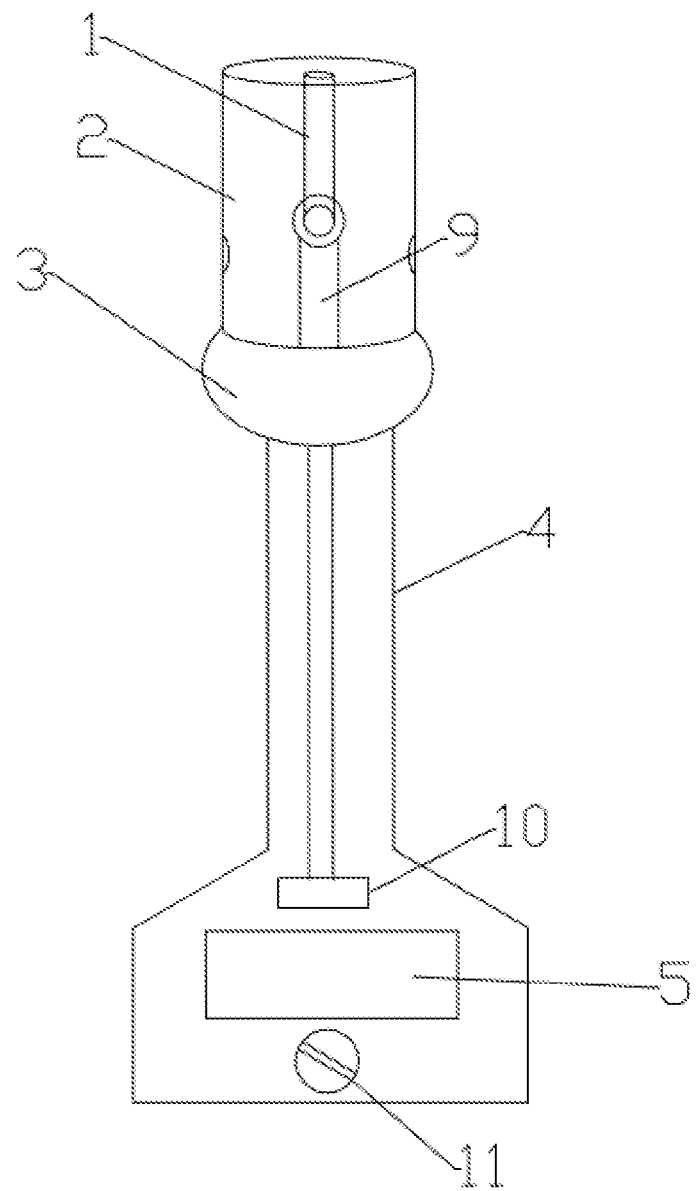
FIG. 1 is the schematic diagram for the overall structure of the proposal.
Figure 2:
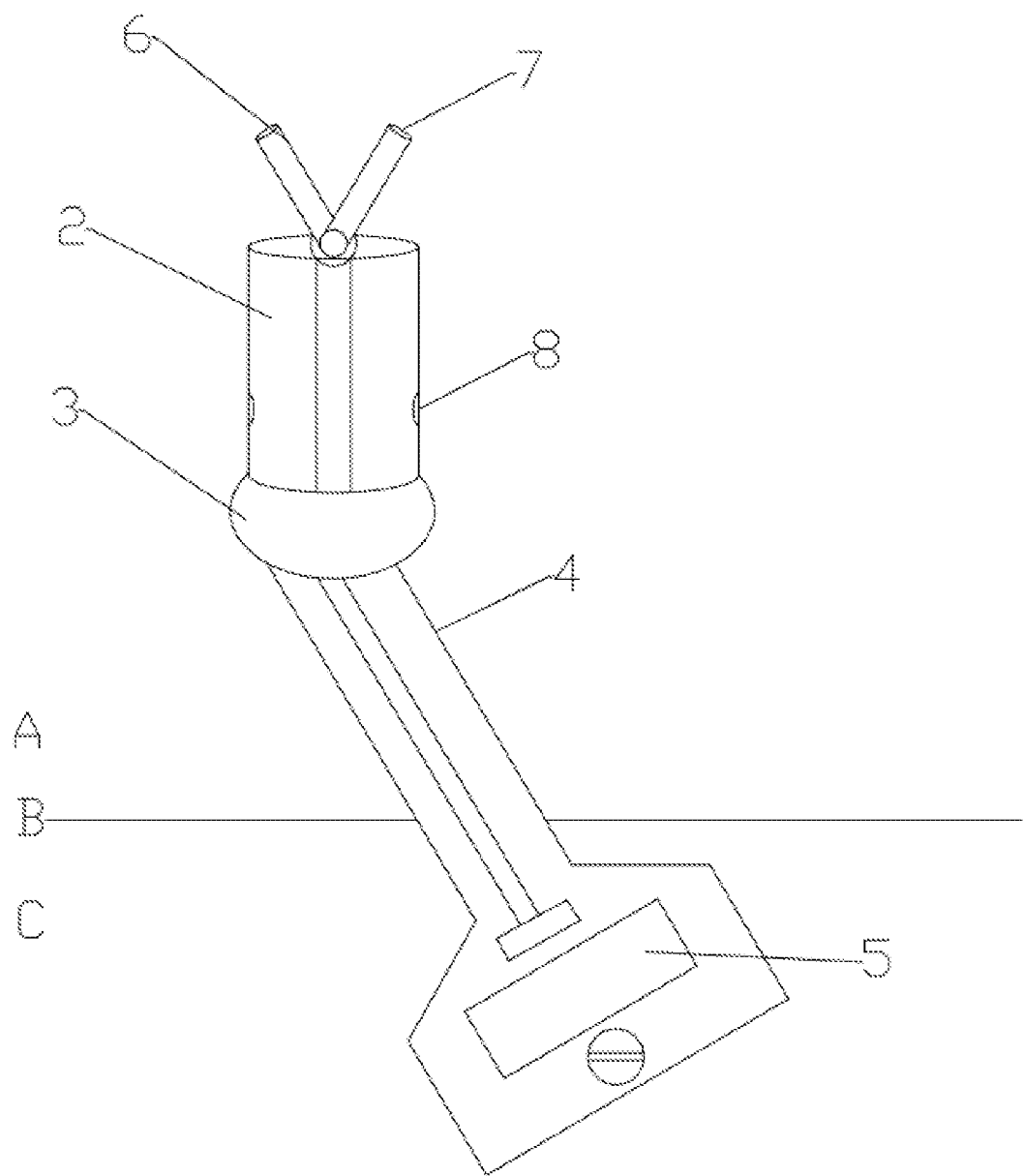
FIG. 2 is the schematic diagram for the use state of the proposal.
Figure 3:
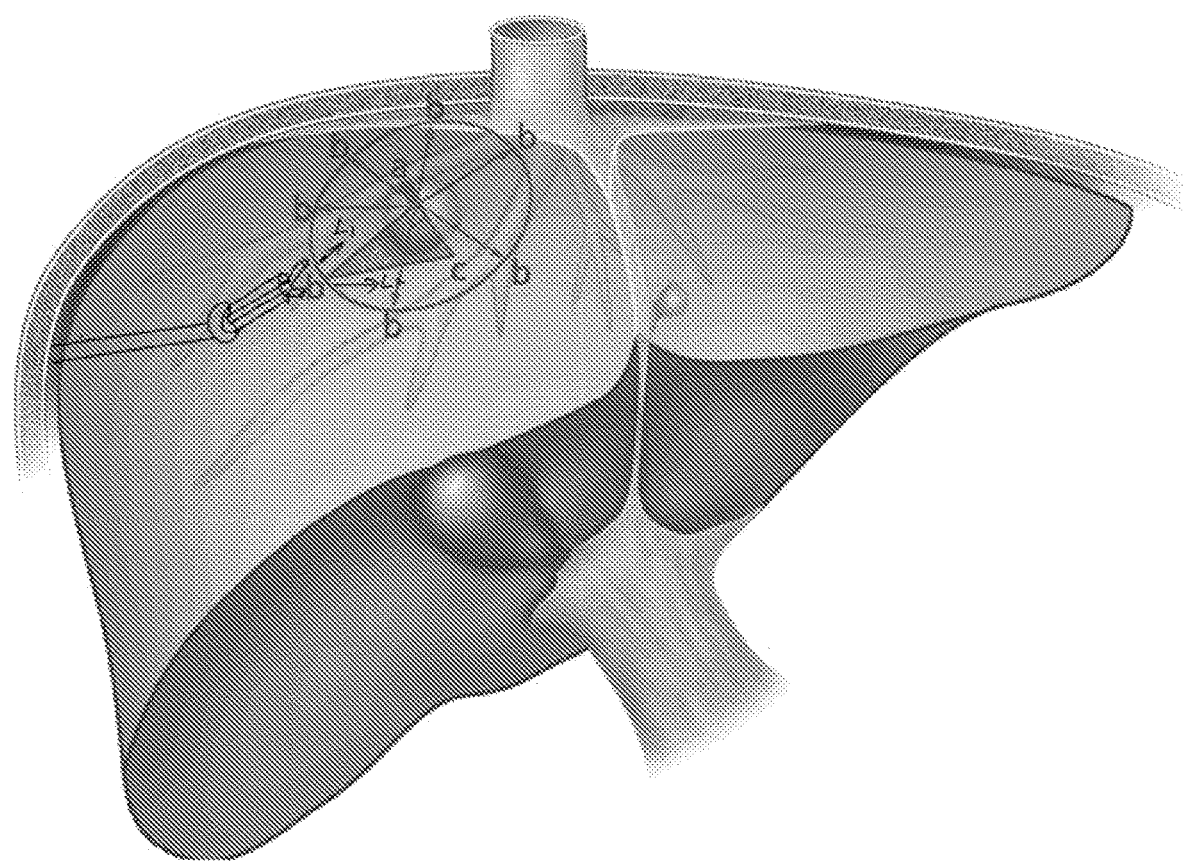
FIG. 3 is the model diagram of the proposal.

As shown in FIG. 1-2, a laser-assisted tumor localization and resection device in the invention comprises a laser displacement sensor, a cylindrical base, a joint part, a transmission rod, and a data screen, wherein the laser displacement sensor comprises sensors L1 and L2, which are revolvably arranged in the cylindrical base and are coaxial. Mounting holes are arranged on both sides of the cylindrical base. The transmission rod is revolvably connected with the cylindrical base at multiple angles through the joint part, and the data screen is arranged on the transmission rod.

Further, an external line connected with the laser displacement sensor is arranged in the transmission rod.

Further, the cylindrical base is hollow and cylindrical, and is 2-4 cm long.

Further, a telescopic rod is arranged in the cylindrical base, and the sensor L1 and the sensor L2 are coaxially arranged on the telescopic rod.

Further, the data screen is provided with a rotary disk, which is connected with a rotary drive device arranged on the sensor L2.

Further, a locking button is arranged on the transmission rod.

Further, the laser displacement sensor is ZLDS10X or ZLDS11X laser displacement sensor, which is 1-2 cm long.

EMBODIMENT

Figure 4:
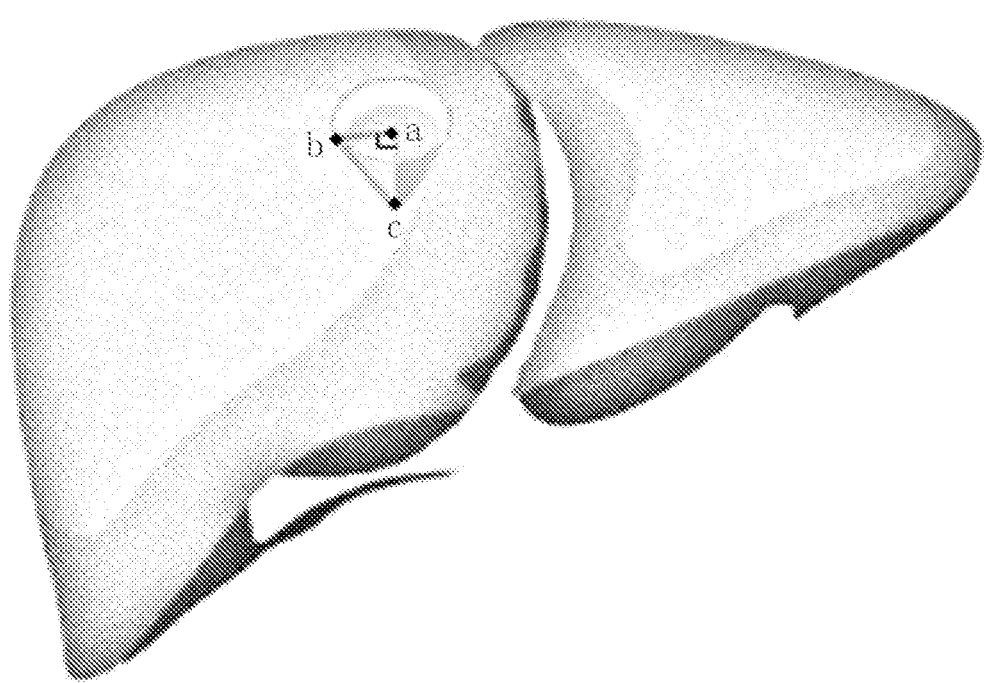
FIG. 4 is the tumor resection diagram of the proposal.

The sensors L1 sensor L2 can emit two beams L1 and L2. The angle of the sensor L2 can be adjusted by rotating the rotary disc so that the laser displacement sensor is turned on, and then the beams L1 and L2 form an included angle α; measure and calculate three side lengths ab/ac/bc and angle α of the triangular model containing the tumor on CT three-dimensional image (by the trigonometric formula $$bc = \frac{ac}{\sin\alpha}, ab = \sqrt{bc^2 - ac^2}\,));$$

determine the point a during operation according to the color ultrasound, and measure the point b by the beam L1 of the laser-assisted device according to the preoperative length ab, select a point as the point b from the circumference with ab as the radius, and fix the cylindrical base of the laser-assisted device on the surface of the organ; adjust the rotary disk according to the included angle α planned preoperatively to make L2 rotate by the angle α in the direction of incision in the liver; incise the liver along the indication point of the beam L2, follow the green point of L2 to incise until the length of the beam L2 entering the liver is the preoperative side length bc, and then incise to the deepest point c; As the included angle α between the beams L1 and L2 always remains unchanged in the resection process, the green point of the beam L2 on the section plane indicates the incision direction, the real-time length of the beam L2 indicates the incision angle, thus realizing the real-time resection navigation; The surface incised at the initial point b fixed by the laser-assisted device is taken as the initial section plane, and the curved section plane of the "bowl" is expanded by a circle with the point c as the center and bc as the radius to achieve the whole resection of the conical body centered on the tumor, as shown in FIG. 4.

The beam L1 measures ab, the beam L2 measures bc, and a laser beam can be formed between the indication point and the light source and is displayed on the section plane to guide the incision angle and display the incision depth in real-time. The lengths of the beams L1 and L2 and the included angle α formed between the beams L1 and L2 can be displayed on the in vitro data screen to guide the direction and depth that the surgeon resects the organ parenchyma. The laser does not directly locate the tumor. Still, it locates the triangular model containing the tumor, realizing the real-time measurement of the distance among the three sides and the included angle α and ensuring the tumor resection according to the preoperatively planned path.

It should be noted that the relational terms such as first and second in the text are only used to distinguish one entity or operation from another entity or operation and do not necessarily require or imply any such actual relationship or order between these entities or operations. Also, the terms "comprise" and "contain" or any other variants are intended to cover non-exclusive "contain" so that the process, method, item, or device comprising a series of elements not only comprises those elements but also comprises other elements not listed clearly or also comprises inherent elements for the process, method or device.

Although the embodiments of the invention have been shown and described, it is understandable for the ordinary technicians in the field that these embodiments can be changed, modified, replaced and varied in various ways without deviation from the principle and spirit of the invention, and the attached claims and their equivalents limit the scope of the invention.

The invention and its embodiments are described above. The description is not restricted, the drawings only show one of the embodiments of the invention, but the actual structure is not so limited. In a word, if the ordinary technicians in the field are inspired by the invention, design structures and embodiments similar to the technical proposal without deviation from the purpose of the invention and without creativity, such structures and embodiments shall be within the scope of protection of the invention.

The invention claimed is:

1. A laser-assisted tumor localization and resection device, which is characterized in that the laser-assisted tumor localization and the resection device comprises a laser displacement sensor, a cylindrical base, a joint part, a transmission rod, and a data screen, wherein the laser displacement sensor comprises sensors L1 and L2, which are revolvably arranged in the cylindrical base and are coaxial, mounting holes are arranged on both sides of the cylindrical base, the transmission rod is revolvably connected with the cylindrical base at multiple angles through the joint part, and the data screen is arranged on the transmission rod, wherein the device is further characterized in that that a line connected to the laser displacement sensor is arranged in the transmission rod, wherein the device is further characterized in that the cylindrical base is hollow and cylindrical, and is 2-4 cm long, wherein the device is further characterized in that a telescopic rod that is arranged in the cylindrical base, and the sensor L1 and the sensor L2 are coaxially arranged on the telescopic rod, and wherein the device is further characterized in that the data screen is provided with a rotary disk, which is connected with a rotary drive device arranged on the sensor L2.

2. A laser-assisted tumor localization and resection device, according to claim 1, which is characterized in that a locking button is arranged on the transmission rod.

3. A laser-assisted tumor localization and resection device, according to claim 2, which is characterized in that the laser displacement sensor is ZLDS10X or ZLDS11X, which is 1-2 cm long.

* * * * *